United States Patent [19]

Heller et al.

[11] 4,011,760
[45] Mar. 15, 1977

[54] MEASURING PROBE FOR GAS MEASURING APPARATUS

[75] Inventors: Dieter Heller; Helmut Hannemann, both of Lubeck, Germany

[73] Assignee: Dragerwerk Aktiengesellschaft, Germany

[22] Filed: Dec. 5, 1975

[21] Appl. No.: 638,171

[30] Foreign Application Priority Data

Dec. 18, 1974 Germany .......................... 2459826

[52] U.S. Cl. .......................................... 73/421.5 R
[51] Int. Cl.² .......................................... G01N 1/22
[58] Field of Search .......... 210/242, 121; 73/421.5, 73/322.5; 222/405

[56] References Cited

UNITED STATES PATENTS

| 2,358,472 | 9/1944 | Owens | 73/322.5 |
| 3,794,446 | 2/1974 | Ost | 210/242 |
| 3,921,457 | 11/1975 | Barnes et al. | 73/421.5 R |

*Primary Examiner*—S. Clement Swisher
*Attorney, Agent, or Firm*—McGlew and Tuttle

[57] ABSTRACT

A measuring probe for a gas measuring apparatus comprises a probe head which is made of a floatable material and which is connected to a probe line for conveying the measured gas and which is provided with one or more intake openings for the gas and a connecting conduit for connecting the openings to the probe line.

4 Claims, 4 Drawing Figures

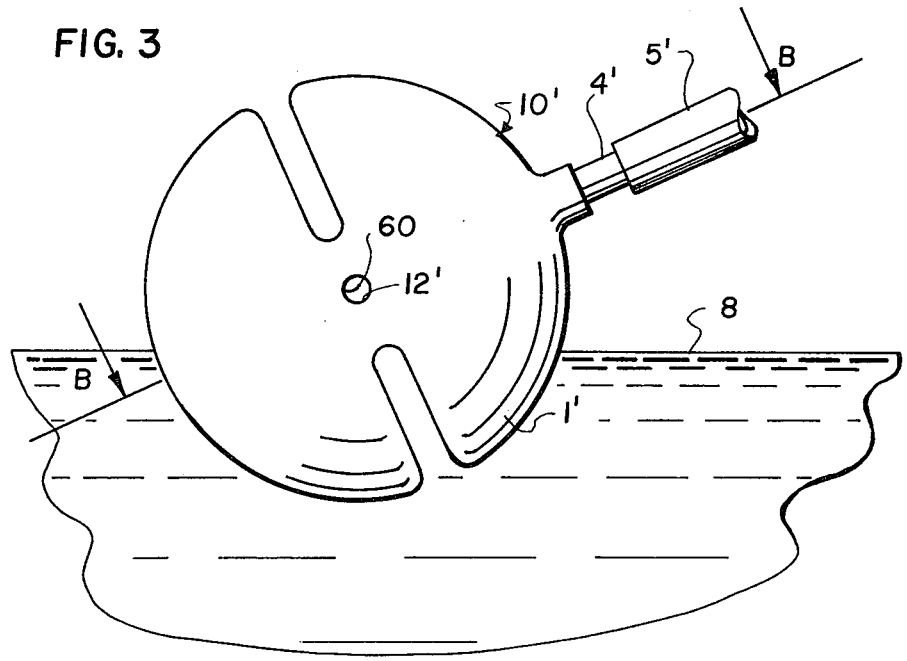
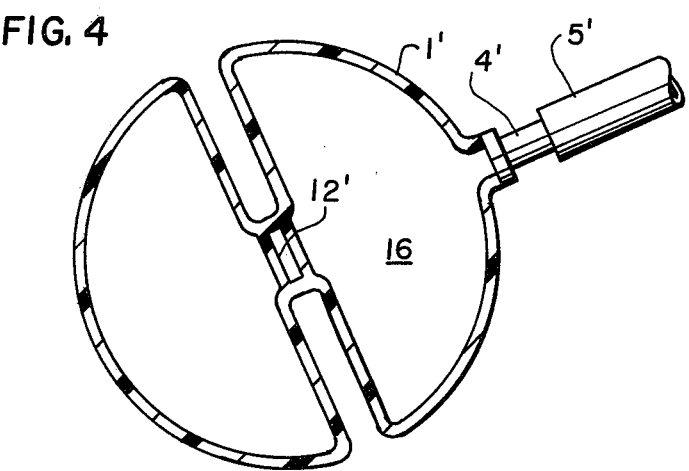

4,011,760

MEASURING PROBE FOR GAS MEASURING APPARATUS

FIELD AND BACKGROUND OF THE INVENTION

This invention relates in general to the construction of a probe intake for gas measuring apparatus and, in particular, to a new and useful floatable probe head having one or more openings therein for the intake of the gas to be measured and an internal connection from the opening to the probe line.

DESCRIPTION OF THE PRIOR ART

The present invention is particularly applicable to a measuring probe for gas measuring apparatus in which a probe head is provided at the end of the probe line for conveying the measured gas to the measuring apparatus. In the known gas measuring devices, standard elastic tubings are used for conveying the gas to be measured and the gas is taken in through the open end of the tubing by means of a pump or other appropriate equipment provided at the measuring device. The tubing is laid up or down to the location where the gas to be measured is to be taken from. Only in cases where the intake opening is observable can it be assured that the intake would not be directed into a liquid zone so that liquid itself may be sucked into the probe line or the measurements would be erroneous in view of the fact that the probe had submerged.

Some known measuring probes are provided with a massive headpiece having a construction which prevents the penetration of liquids in cases where the atmosphere above the liquid surfaces is to be measured. The headpiece can be unscrewed and the probe can then be used as an ordinary tubular probe. A measuring probe with such a massive headpiece requires an observation of the intake because the probe can be lowered only up to the contact with the liquid surface. Upon plunging into the liquid, which is possible in view of the weight of the headpiece, liquid can penetrate therein.

SUMMARY OF THE INVENTION

The present invention provides a probe by means of which gas to be measured can be conveyed to the gas measuring apparatus through a probe line which is connected to draw off the ambience immediately above a liquid surface without risking a penetration of the liquid into the probe. In accordance with the invention, the probe is provided with a probe head which is designed as a float having one or more intake openings for the gas to be measured and which are located above the liquid surface and which communicate with a connecting piece or line which is adapted to be connected to the probe line.

The main advantage obtained by the invention is that now the gas to be measured can be securely taken in even at uncontrollable locations above the liquid surfaces. The risk of penetration of the liquid into the measuring probe is securely prevented. For measuring purposes, the probe can, for example, be lowered through any cover grating, and the probe head will always float on the liquid surface. Another advantage is that the gas to be measured is in all cases securely withdrawn immediately above the surface of the liquid. This can be of importance for the detection and determination of the concentration of the gas to be measured.

According to a further development of the invention, the float is designed as a body of foamed plastic in which a piece of pipe providing the intake openings, and connected to a connecting piece, is embedded. In a further development of the invention, the piece of pipe may comprise a tee-piece. With this design, the inventive device is secure in operation and, in addition, can be manufactured in a simple manner. In consequence, a method of manufacturing is provided according to which the foam material is foamed around the piece of pipe to form a foamed plastic body which will float. In a design which is particularly simple in manufacture and, thereby inexpensive, the probe head is a spherical part injection-molded of a plastic.

Accordingly, it is an object of the invention to provide a probe head comprising a probe body which is made of a floatable material having at least one opening therein with a connection through the interior of the probe to a probe line for the collected gas.

A further object of the invention is to provide a probe head which comprises a T-shape fitting having a foamed plastic formed therearound and which includes an open end at each end of the head of the T and a central connection line from the T to the probe line for the transfer of the gases to the probe.

A further object of the invention is to provide a probe which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there are illustrated preferred embodiments of the invention.

BRIEF DESCRIPTION OF THE DRAWINGS

In the Drawings:

FIG. 3 is a view similar to FIG. 1 of another embodiment of the invention; and

FIG. 4 is a section taken along the line B—B of FIG. 3.

DESCRIPTION OF THE PREFERRED EMBODIMENTS

Figure 1:
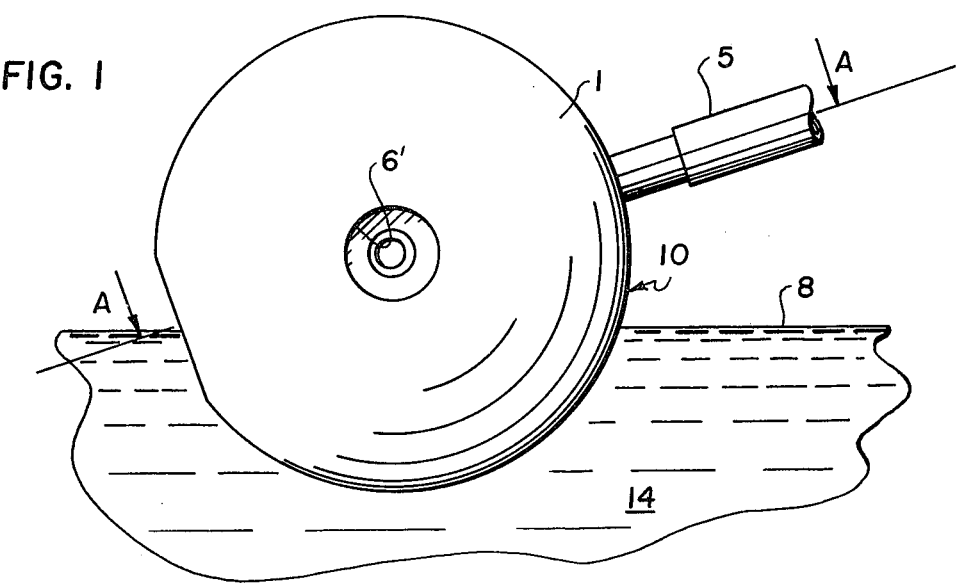
FIG. 1 is a side elevational view of a probe constructed in accordance with the invention.
Figure 2:
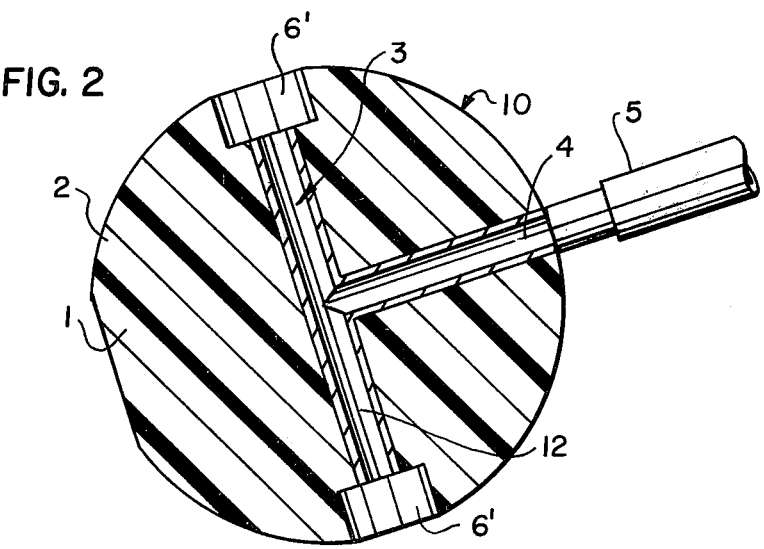
FIG. 2 is a section taken along the line A—A of FIG. 1, but with the parts rotated at an angle in respect to the position shown in FIG. 1.

Referring to the drawings in particular, the invention embodied therein in FIG. 1, comprises a probe, generally designated 10, which includes a probe body 1, made of a floatable material, such as foamed plastic, and which has one or more openings 6, 6' which communicate through a cross-passage 12 of a pipe, generally designated 3', to a longitudinal passage 4 which connects to the probe line 5 for the gases to be tested. Probe line 5 extends to a gas measuring apparatus, which is not shown. The gas to be measured is taken in through the intake openings 6 or 6'. The shape of the float ensures that even if it is positioned on a liquid 14 with one of the openings 6' submerged in the water, the other opening 6 will still be above the water in a position such that the gas immediately above the surface of the water will flow freely through the opening 6' in the cross-pipe section 12 to the connection 4 to the probe line 5. At least one opening 6 always remains above the surface 8 of the liquid and the material of the body 2 is sufficiently light that the float will always float high enough to maintain a connection between the cross-passage 12 and the longitudinal passage 4. A probe head 10 is advantageously made with a body portion 1 formed by a foamed plastic material 2 which is foamed over the T-shaped pipe connection 3.

In the embodiment shown in FIGS. 3 and 4, there is a probe, generally designated 10', having a float or body portion 1' which comprises a single piece of an injection molded plastic material defining a hollow interior chamber 16 which communicates through a nipple fitting 4' to a probe line 5' similar to the other embodiment. In this case body 1' is provided with an opening 60 at each side which communicates through a cross-passage 12' to the interior chamber 16 which is in communication with nipple 4' and the probe line 5'.

While specific embodiments of the invention have been shown and described in detail to illustrate the application of the principles of the invention, it will be understood that the invention may be embodied otherwise without departing from such principles.

What is claimed is:

1. A measuring probe for gas measuring apparatus, comprising a probe head, a probe line for conveying the measured gas to the gas measuring apparatus connected into said probe head, said probe head comprising a float having at least one intake opening for the measured gas, and a connecting passage connected between the opening and said probe line, a pipe located within said probe head, said probe head being a foamed plastic material, said pipe defining the passage connected between the opening and said probe line, said pipe comprising a T-shape piece.

2. A measuring probe for gas measuring apparatus, according to claim 1, wherein said probe head comprises a spherical member made of injection-molded plastic.

3. A measuring probe for gas measuring apparatus, comprising a probe head, a probe line for conveying the measured gas to the gas measuring apparatus connected into said probe head, said probe head comprising a float having at least one intake opening for the measured gas, and a connecting passage connected between the opening and said probe line, said probe including a pipe forming said connecting passage and comprising a T-shape piece, said probe comprising a foam material foamed over said pipe, said T-shape pipe having a transverse passage opening at each side of said probe.

4. A measuring probe for gas measuring apparatus, comprising a probe head, a probe line for conveying the measured gas to the gas measuring apparatus connected into said probe head, said probe head comprising a flat having at least one intake opening for the measured gas, and a connecting passage connected between the opening and said probe line, said probe comprising a hollow spherical part having a transverse passage extending therethrough communicating with the interior of said probel, said interior comprising a connection passage to said probe line.

* * * * *